United States Patent [19]

Yokoi et al.

[11] Patent Number: 4,957,112
[45] Date of Patent: Sep. 18, 1990

[54] ULTRASONIC DIAGNOSTIC APPARATUS

[75] Inventors: Takeshi Yokoi, Hachioji; Tsuguhisa Sasai; Kenji Hirooka, both of Tokyo, all of Japan

[73] Assignee: Olympus Optical Co., Ltd., Tokyo, Japan

[21] Appl. No.: 272,464

[22] Filed: Nov. 17, 1988

[30] Foreign Application Priority Data

Nov. 20, 1987 [JP] Japan .................................. 62-176500
Dec. 26, 1987 [JP] Japan .................................. 62-331519
Dec. 28, 1987 [JP] Japan .................................. 62-330292

[51] Int. Cl.⁵ ............................................. A61B 8/12
[52] U.S. Cl. .................................... 128/662.06; 128/4
[58] Field of Search ........................... 128/622.06, 4, 6

[56] References Cited

U.S. PATENT DOCUMENTS

| 4,375,818 | 3/1983 | Suwaki et al. | 128/662.06 |
| 4,391,282 | 7/1983 | Ando et al. | 128/662.06 |
| 4,466,443 | 8/1984 | Utsugi | 128/662.06 |

Primary Examiner—Francis Jaworski
Attorney, Agent, or Firm—Stevens, Davis, Miller & Mosher

[57] ABSTRACT

An ultrasonic diagnostic apparatus including an ultrasonic vibrating element, a rotator for rotating the ultrasonic vibrating element, an illuminating window and an observing window arranged in a side wall of an inserting portion. The apparatus is so arranged that the center axis of the inserting portion is deviated from that of the rotator with respect to the radial direction but the center of curvature of a cover window surrounding the rotator is coincident with the center axis of the rotator. Therefore, a uniform resolving power can be obtained in all directions into which the ultrasonic wave is transmitted. Then an ultrasonic image without undesired artificates is displayed on a screen of a monitor and the outer diameter of the inserting portion can be made small.

12 Claims, 10 Drawing Sheets

FIG_1A
PRIOR ART

FIG_1B
PRIOR ART

FIG_1C
PRIOR ART

FIG_1D
PRIOR ART

FIG.2
PRIOR ART

FIG_3

FIG_4F

FIG_4G

FIG_4H

FIG_7

ULTRASONIC DIAGNOSTIC APPARATUS

BACKGROUND OF THE INVENTION

Field of the Invention and Related Art Statement

This invention relates to an ultrasonic diagnostic apparatus having an ultrasonic vibrating element arranged in an inserting portion thereof to scan an object to be inspected in order to obtain an ultrasonic image of the object, and more particularly, to an ultrasonic diagnostic apparatus having an endoscope by which an optical image of the object can be also obtained.

In the ultrasonic diagnostic apparatus, there are provided the ultrasonic vibrating element at a distal end of the inserting portion and a rotator to scan the object with the ultrasonic wave generated by the element in the direction that crosses at right angles with respect to the center axis of the inserting portion. A cover is arranged to surround the rotator, which serves as a window through which the ultrasonic wave transmits, and the space formed between the rotator and the cover is filled with an ultrasonic propagating medium such as water and liquid paraffin.

Figure 1A:
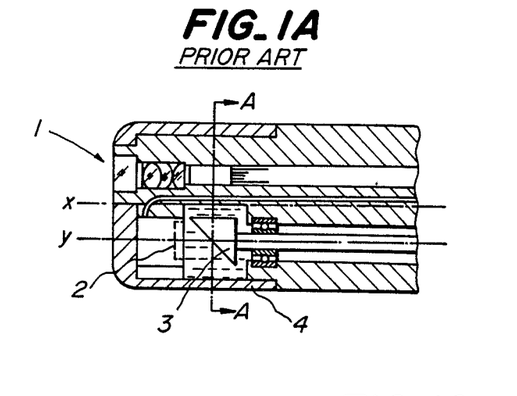
FIG. 1A is a schematic view showing a cross section of the distal end portion of the inserting portion of the conventional ultrasonic diagnostic apparatus.
Figure 1B:
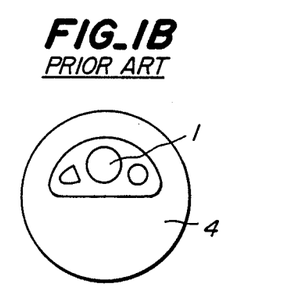
FIG. 1B is a front view showing the distal end portion of the conventional apparatus illustrated in FIG. 1A.
Figure 1C:
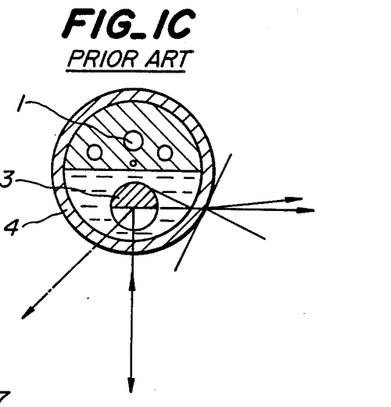
FIG. 1C is a cross-sectional view cut along A—A line of FIG. 1A.

In Japanese Utility Model Publication Kokai Sho No. 58-136,106, there is disclosed a known ultrasonic diagnostic apparatus. FIG. 1A is a cross-sectional view showing a distal end portion of an inserting portion of the conventional ultrasonic diagnostic apparatus, FIG. 1B is a front view thereof and FIG. 1C is a cross-sectional view showing the section cut along A—A line in FIG. 1A. As apparent from these figures, the conventional ultrasonic diagnostic apparatus is formed as so-called forward view type, therefore a center axis y of a rotator 3 serving as a mirror on which an ultrasonic wave emitted from an ultrasonic vibrating element 2 is reflected, is deviated from a center axis x of the inserting portion of the apparatus, and there is provided an observing optical system 1 beside the rotator 3. A cover 4 surrounding the rotator 3 also forms a part of the circumferential surface of the inserting portion and a portion of the cover constitutes a window through which the ultrasonic wave reflected by the mirror 3 exits and ultrasonic wave reflected by the object is made incident upon the mirror.

Figure 1D:
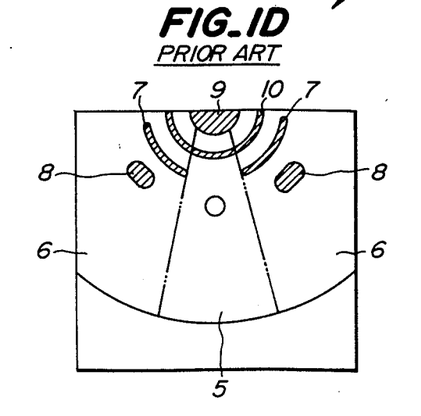
FIG. 1D is a schematic view illustrating an example of the ultrasonic image of the object indicated on the monitor by using the known ultrasonic diagnostic apparatus shown in FIGS. 1A-1C.

Such conventional ultrasonic diagnostic apparatus has the following problems. That is to say, since the circumferential surface of the cover 4 also serves to form the circumferential surface of the inserting portion, the center axis of the curvature of the cover is coincident with the center axis x of the inserting portion but is deviated from the center axis y of the rotator 3. Under such construction, the distance between the cover 4 and rotator 3 (reflecting mirror), and the incident angle of the ultrasonic wave with respect to the cover 4 vary in dependent on a point of the cover 4 where the ultrasonic wave exits and enters from and into the inserting portion. FIG. 1D is a schematic view illustrating an ultrasonic image displayed on a screen of a monitor formed by the conventional ultrasonic diagnostic apparatus. As shown in FIG. 1D, in case the ultrasonic wave propagates through the cover 4 in an area 5, where the incident angle would be not so large, there is no undesired artifact (multiple echo) and a high azimuth resolution can be obtained. But, in case the ultrasonic wave propagates in an area 6, where the incident angle would be large, there is recognized artifacts 7 caused by refraction and reflection of the ultrasonic wave, and the azimuth resolution becomes low. For example, the circular-shaped object is indicated as an elliptical 8 on the monitor due to the refraction of the ultrasonic wave. In FIG. 1D, the numerical number 9 represents the circumference surface of the cover 4 and the numerical number 10 represents a normal artifact.

Figure 2:
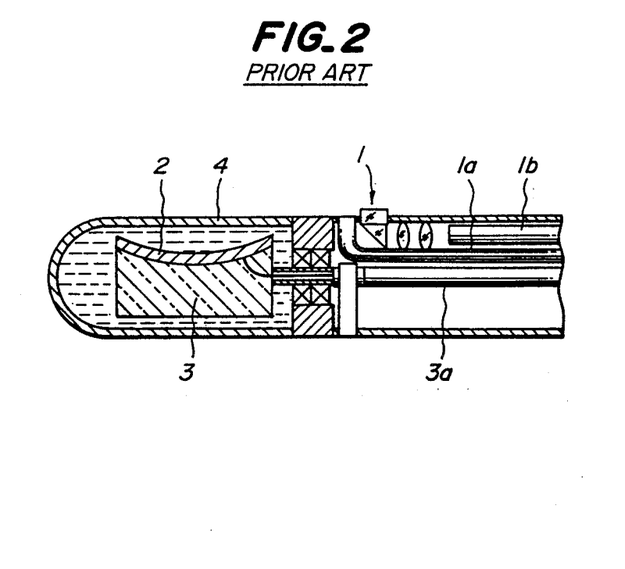
FIG. 2 is a cross-sectional view showing the distal end portion of the inserting portion of another conventional ultrasonic diagnostic apparatus.

Contrary to the above, in a specification of U.S. Pat. No. 4,572,201, there is disclosed an ultrasonic diagnostic apparatus in which the center axis of the curvature of the cover surrounding the rotator is arranged to be coincident with the center axis of the rotator. FIG. 2 is a cross-sectional view illustrating the distal end of the inserting portion of this apparatus. However, in this apparatus, a central axis of the inserting portion, the rotating axis of the rotator 3 and the center axis of the curvature of the cover 4 are arranged on the same axis, as clear from FIG. 2. In the inside of the inserting portion of the apparatus, it is necessary to arrange a light guide 1a constituting the illuminating system and an image guide 1b constituting the observing system (or a signal cable in case that a solid state image sensor is used), these elements extending from the distal end of the inserting portion to an operational portion of the apparatus, besides a shaft 3a extending from a rotator 3 on which an ultrasonic element 2 is provided to a sub-operational portion. In this case, since the shaft 3a is coincident with the rotating axis of the rotator 3, there would be formed a wasteful space in which the light guide 1a and the image guide 1b are not arranged, and the outer diameter of the inserting portion of the apparatus as a whole becomes thick. Thus, there is a drawback that the inserting portion cannot be inserted into a cavity of living body easily.

Further, in case that the observing system comprises a solid state image sensor, it is necessary to arrange two signal cables, one of them is extended from the solid state image sensor and the other is extended from the ultrasonic element, both of which are connected to an external controlling device v-a the operational portion of the apparatus. However, since these two cables of the conventional apparatus are arranged so closely to each other in the inserting portion, when the solid state image sensor and the ultrasonic element are driven at the same time they would be influenced by each other and the inductive noises are generated in both cables. Therefore, there are appeared noises on one or both of the optical image and ultrasonic image displayed on the screen of the monitor and highly qualified images cannot be obtained.

SUMMARY OF THE INVENTION

The present invention has for its primary object to provide a mechanical scanning type ultrasonic diagnostic apparatus in which a uniform resolving power can be obtained with respect to all directions in which the ultrasonic wave exits from the cover and there is displayed no improper artifact on the screen of the monitor, and thus a highly qualified image can be obtained without a complicated structure.

In order to carry out the primary object, the ultrasonic diagnostic apparatus according to the invention comprises:
   an inserting portion having distal and proximal ends;
   an ultrasonic wave transmitting and receiving means having an ultrasonic vibrating element arranged at the distal end of the inserting portion for transmitting and receiving an ultrasonic wave for scanning an object to be inspected along with a plane that crosses at substantially right angles with respect to an axis of the inserting portion;

a cover arranged at the distal end of inserting portion and having a window through which the ultrasonic wave transmitted by said ultrasonic vibrating element exits toward the object and the ultrasonic wave reflected by the object is made incident upon said ultrasonic vibrating element;

a rotating means connected to said ultrasonic wave transmitting and receiving means for rotating at least a part of said ultrasonic wave transmitting and receiving means to scan the object;

an illuminating system for illuminating the object; and an observing system for forming an optical image of said object; whereby the axis of said inserting portion is arranged to be deviated from a rotating axis of said ultrasonic wave transmitting and receiving means in a radial direction; and a center of curvature of said window is arranged to be coincident with the rotating axis of said ultrasonic wave transmitting and receiving means.

In the ultrasonic diagnostic apparatus according to the invention, a uniform resolving power can be obtained in all radial directions and a highly qualified image can be also obtained which has no undesired artifact due to the refraction and reflection of the ultrasonic wave.

The present invention has for the second object to provide an ultrasonic diagnostic apparatus, wherein the observing system comprises a solid state image sensor, by which low-noise optical and ultrasonic images can be obtained on the screens of the monitors even if the solid state image sensor and the ultrasonic vibrating element are driven at the same time.

In order to achieve the second object, in the ultrasonic diagnostic apparatus according to the present invention, the first signal cable extending from the solid state image sensor along the inserting portion and the second signal cable extending from the ultrasonic vibrating element in parallel with said first signal cable are arranged such that the core conductors of these cables are placed diagonally opposite positions viewed in a plane which is perpendicular to the axis direction of the inserting portion.

DETAILED DESCRIPTION OF PREFERRED EMBODIMENTS

Figure 3:
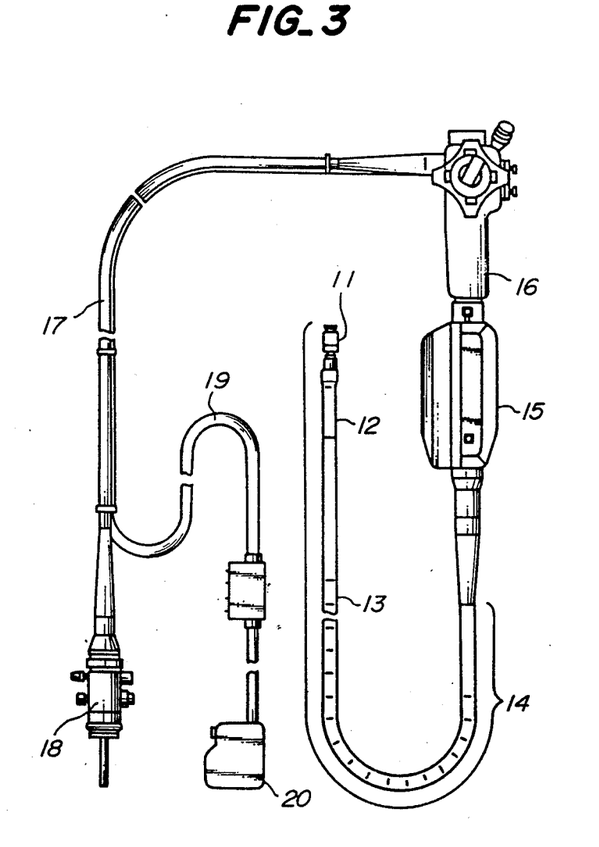
FIG. 3 is a schematic view illustrating the general construction of the ultrasonic diagnostic apparatus according to the present invention.

FIG. 3 is a schematic view showing the whole construction of the ultrasonic diagnostic apparatus according to the present invention.

As shown in FIG. 3, an inserting portion 14 comprises a distal end portion 11, a bending portion 12 and a flexible portion 13 continuously in this order. An ultrasonic operating portion 15 having a rotator driving means for rotating a rotator arranged in said distal end portion of the inserting portion, and an endoscope operating portion 16 having a handle for bending the bending portion 12, an air and water supply device and a suctioning device is connected to the ultrasonic operating portion. An endoscope connector 18 is connected to the endoscope operating portion 16 via a universal cord 17. An electric cable cord 19 is branched from said universal cord 17, and an electric connector 20 is connected to the endoscope operational portion via said universal cord 17 and said electric cable cord 19. The endoscope connector 18 is connected to a video processor (not shown) to display an optical image of the object on a screen of a monitor, and the electric connector 20 is connected to an ultrasonic wave observing device (not shown) to display an ultrasonic image of the object.

FIGS. 4A-4G are schematic views showing the internal construction of the distal end portion 11 of the inserting portion 14 of the present apparatus.

Figure 4A:
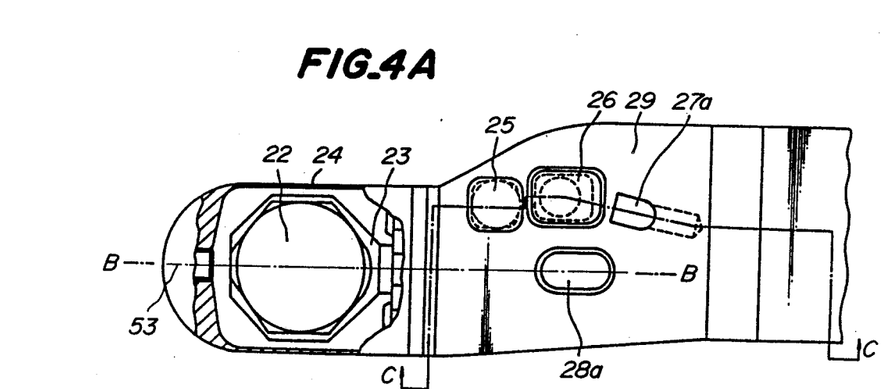
FIGS. 4A-4H are schematic views representing a first embodiment of the ultrasonic diagnostic apparatus according to the present invention.
Figure 4B:
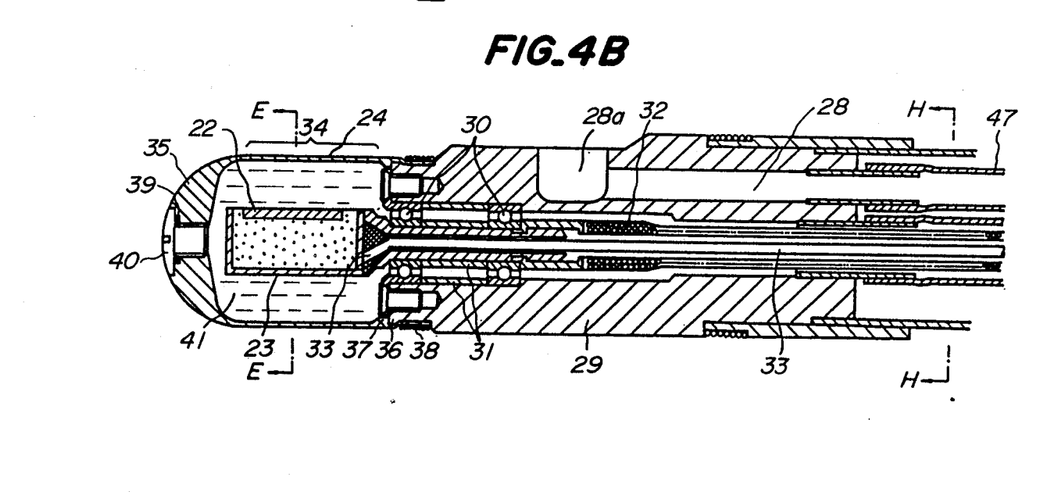
Figure 4C:
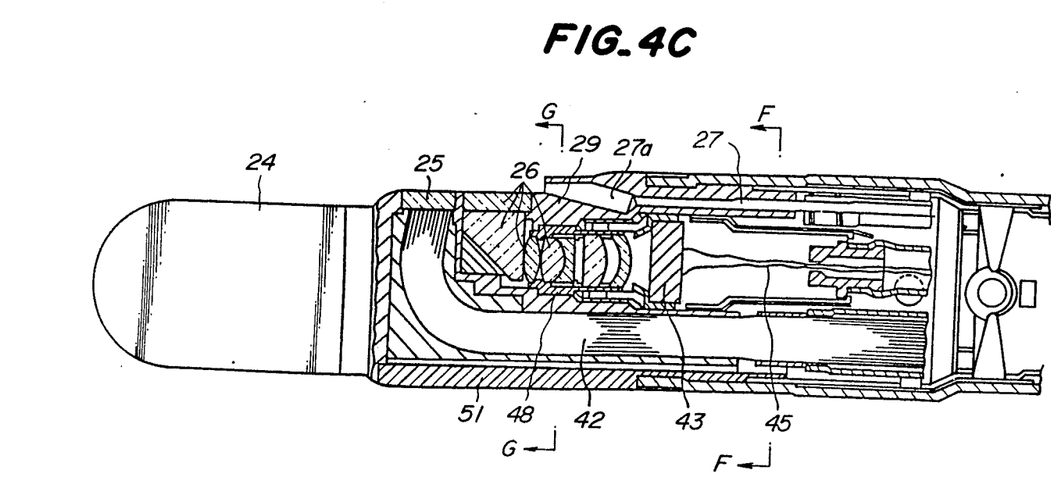
Figure 4D:
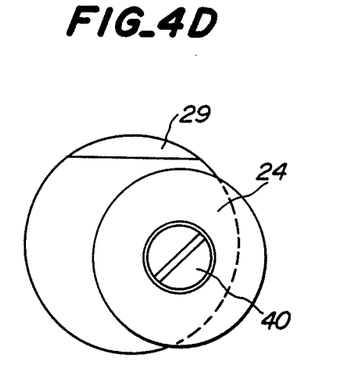
Figure 4E:
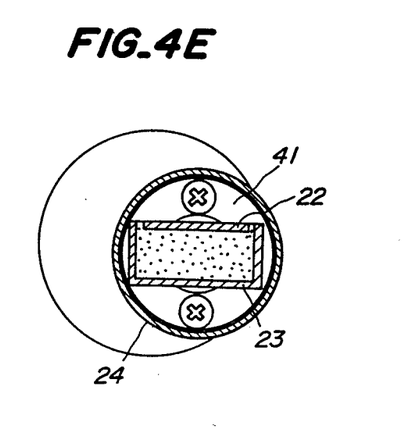
Figure 4F:
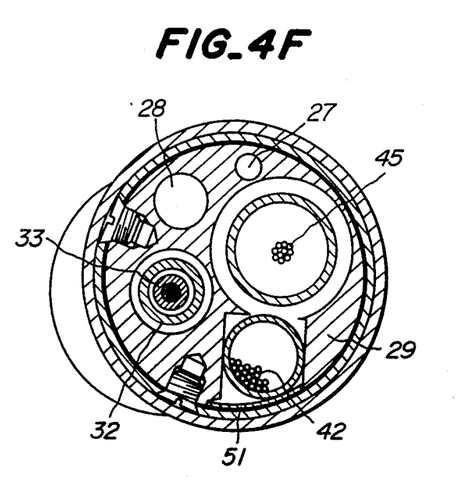
Figure 4G:
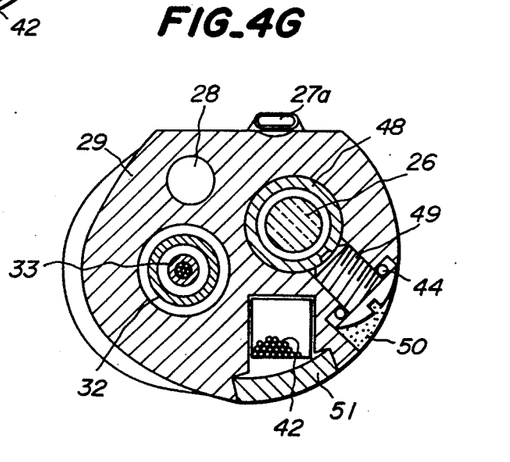
Figure 4H:
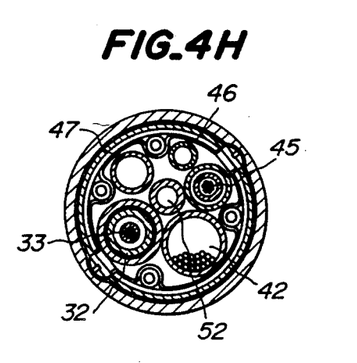

FIG. 4A is a side view showing the distal end portion 11 of the inserting portion 14 a part of which is illustrated as a cross-sectional view. FIG. 4B is a cross-sectional view cut along B—B line in FIG. 4A; FIG. 4C is a cross-sectional view cut along C—C line in FIG. 4A; FIG. 4D is a front view showing the distal end portion of the apparatus; FIG. 4E is a cross-sectional view cut along E—E line in FIG. 4B; FIG. 4F is a cross-sectional view cut along F—F line in FIG. 4C; FIG. 4G is a cross-sectional view cut along G—G line in FIG. 4C; and FIG. 4H is a cross-sectional view cut along H—H line in FIG. 4B.

A rotator 23, in which an ultrasonic vibrating element 22 is incorporated via an ultrasonic absorbing material, is arranged t the distal end portion 11 and a cover 24 is arranged to surround the rotator 23. As shown in FIGS. 4B and 4E, there is provided a window 34 which is integrally formed with the cover 24 made by thin hard polyethylene sheet, through which an ultrasonic wave exits and enters with respect to the inserting portion. And a space formed between the cover 24 and the rotator 23 is filled with an ultrasonic propagating medium 41, e.g. a liquid paraffin. In the external surface of the hard top portion 29 of the inserting portion, there are provided an illuminating lens 25, an objective lens system 26, an air and water supply nozzle 27a, and a suction hole 28a. As shown in FIG. 4C, an exit end of a light guide fiber 42 constituting the illuminating system is arranged to be opposite to the illuminating lens 25, and a solid state image sensor 43 is arranged to be opposite to the objective lens system 26. The light guide fiber 42 and a signal cable 45 connected to the solid state image sensor 43 are extended through the inserting portion up to the endoscope connector 18.

The rotator 23 is supported by the top hard portion 29 via bearings 30 and a spacer 31. The back portion of the rotator 23 is connected to a flexible driving shaft 32 by which a rotation driving power generated by a motor provided in the ultrasonic operational portion 15 is transmitted. A signal cable 33 is extended from the ultrasonic vibrating element 22 to the electric connector 20 through the inside of the driving shaft 32 with respect to the axis direction of the inserting portion. As shown in FIG. 4A, the upper portion of the outer circumference of the cove 24 is depressed from the outer circumference of the hard portion 29 viewed in the direction in which the rotating axis of the rotator 23 is shifted from the center axis of the inserting portion 14, and the outer circumference of the cover 24 is also depressed from the outer circumference of the hard portion 29 viewed in the directions which cross at right angles to said shifting direction. Furthermore, in FIG. 4A the lower portion of the outer circumference of the cover 24 is projected a little from the outer circumference of the cover 24 viewed in said shifting direction. Thus, the cover 24 is formed in such manner that the diameter thereof is smaller than that of the hard portion 29. It should be noted that the cover 24 is coupled with the hard top portion 29 via a smoothly curved surface. The cover 24 constitutes a window 34 through which the ultrasonic wave exits and enters with respect to the inserting portion, a cover top 35 formed like a bullet head, and a ring-shaped perfection 37 which is engaged with an edge 36 of the top hard portion 29 of the inserting portion. The cover 24 is secured to the top hard portion 29 by winding a string 38. In the top of the cover 24, a blind screw 40 is provided via an O-ring 39 to seal the ultrasonic propagating medium 41 filled in the space within the cover. The head surface of the blind screw 40 is polished by buffing into alignment with the curved outer surface of the top of the cover 24. The light guide fiber 42, which is extended from the inserting portion 14 to the endoscope connector 18, is optically connected to the illuminating lens 25. The optical image obtained by the objective lens 26 is formed on the solid state image sensor 43 and photoelectrically converted to an electric signal, and the electric signal is supplied to the video processor (not shown) by the signal cable via the endoscope connector 18. In FIG. 4F, the numerical number 46 represents the air and water supply tube and the numerical number 47 represents a suction tube. As shown in FIG. 4G, a frame 48 for holding the objective lens 26 is fixed to the top hard portion 29 by a screw 49 via an O-ring 44, and a sealing agent 50 is applied on the head of the screw 49. And also, the light guide fiber 42 is arranged within a light guide cover 51.

As explained above, and as apparent from FIGS. 4A-4G, in the apparatus according to the present invention, the rotating axis 53 of the rotator 23 is deviated from the center axis of the inserting portion 14 but coincident with the center axis of the cover 24.

Since the rotating axis 53 of the rotator 23 is coincident with the center of curvature of the cover 24, the incident angle of the ultrasonic beam to the cover 24 becomes zero at every positions. Therefore, the ultrasonic wave is transmitted the window 34 always perpendicularly, and thus the image having a uniform resolving power can e obtained without influence of the cover 24.

FIG. 4H is a cross-sectional view cut along H—H line in FIG. 4B. The first signal cable 45 extending from the solid state image sensor 43 along the axis direction of the inserting portion 14 and the second signal cable 33 extending from the ultrasonic vibrating element 22 in parallel with said first signal cable 45 are so placed that the core conductors of the respective cables are placed at diagonally opposite positions viewed in a plane which crosses the inserting direction of the inserting portion 14 at substantially right angles. Furthermore, there is provided a water supply tube 52 between said first and second signal cables to keep them separate from each other. The light guide fiber 42, the suction tube 47 and the air and water supply tube 46 are arranged in the predetermined places and keeps the positional relationship thereamong.

Since the inner part of the inserting portion 14 is constructed as stated above, the first and second signal cables 45 and 33 are placed as far as possible. Therefore, the induced noises that had been influenced from each other in the conventional apparatus would be remarkably reduced in the apparatus according to the present invention. Thus, even if the solid state image sensor 43 and the ultraonsic vibrating element 22 are driven at the same time and the optical image and ultrasonic image are displayed on the screens of the monitor at the same time, optical and ultrasonic images which are not influenced by noises can be obtained. Also, as shown in FIG. 4H, since the first and second cables 45 and 33, the water supply tube 52, the suction tube 47 and the air and water supply tube 46 are kept in position at least in the inserting portion, if the endoscope is used and the inserting portion is bent, the distance between the first and second signal cables is not shortened because the water supply tube 52 serves as a rigid spacer. Thus, no noises would be generated and highly qualified images can be obtained.

The function of the present invention will be explained in the follow in comparison with the conventional ultrasonic diagnostic apparatus with reference to FIGS. 5A-5D.

Figure 5A:
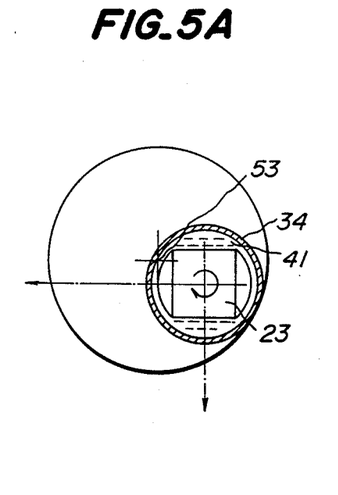
FIGS. 5A-5D are schematic views for explaining the function of the present invention in comparison with the conventional apparatus.
Figure 5B:
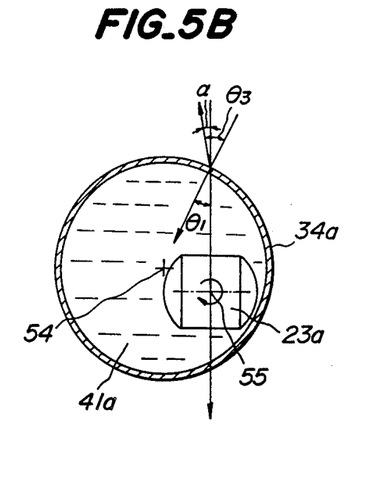
Figure 5C:
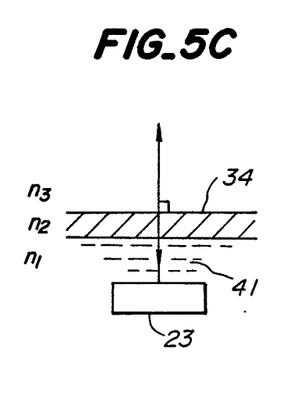
Figure 5D:
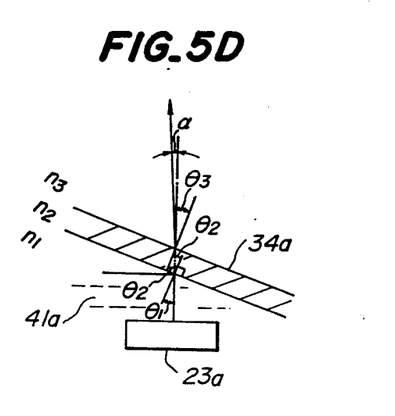

FIGS. 5A-5D are schematic views showing the existence of the deviation between the incident angle and the exit angle of the ultrasonic wave with respect to the surface of window 34 provided in the cover 24. FIGS. 5A and 5C show the present invention and FIGS. 5B and 5D illustrate the conventional apparatus. In the conventional apparatus, since the center 54 of the curvature of the cover 34a is deviated from the rotating axis 55 of the rotator 23a there is formed an inclination between the emitted ultrasonic beam and the inner and outer surfaces of the window 34a, when the ultrasonic beam emits into the space through the window. And thus, the incident angle $\theta_1$ does not become zero. Therefore, there is formed a deviation angle $\alpha$ between the exiting direction of the ultrasonic beam and the incident angle $\theta_1$ ($\alpha = \theta_3 - \theta_1$).

This will be proved by considering the equation of the boundary condition of $n_1 \sin\theta_1 = n_2 \sin\theta_2$. (wherein, $n_1$ and $n_2$ represent refractive indices, $\theta_1$ represents an incident angle, $\theta_2$ represents an exiting angle.) For example, under the condition that a first ultrasonic propagating medium filled in the space is an oil ($n_1 = 1.48$), a material of the window 34 is a plastic ($n_2 = 1.49$), and a second ultrasonic propagating medium between the window 34a and the wall of cavity of the living body is a water ($n_3 = 1.33$), if the incident angle $\theta_1$ of the ultrasonic beam is 20°, the deviated angle $\alpha$ becomes 2.4°, while, if the incident angle $\theta_1$ is 10°, the deviation angle $\alpha$ becomes 1.1°. Therefore, the ultrasonic image of the object is displayed at the place a little deviated from the proper place on the screen of the monitor. And, when the image formed by the ultrasonic beam having the incident angle $\theta_1$ of 20° and the image formed by the ultrasonic beam having the incident angle $\theta_1$ of 10° are displayed in the mutually overlapped manner on the screen, the resolving power will be decreased. In addition to this, there are appeared artifacts because the reflected and incident ultrasonic beam is inclined with respect to the exiting ultrasonic beam due to the refraction at the window 34a.

Contrary to the above, in the present invention, as shown in FIGS. 5A and 5C, the ultrasonic beam always emits perpendicularly to the window 34. Therefore, there is no deviation between the emitting beam and the incident beam and no inclination of the incident beam with respect to the normal line to the surface of the window 34. Thus, the uniform resolving power can be obtained over 360° scanning range.

In the first embodiment of the present invention, as clear from FIG. 4, the shaft 32 connected to the rotator 23, the light guide fiber 42 constituting the illuminating system and the cable 45 connected to the solid state image sensor 43 constituting the observing system are arranged so as to be opposite to each other. Therefore, it is possible to make the outer diameter of the top portion of the inserting portion 14 smaller than that of the apparatus in which those are arranged in line, for example, one diameter of the inserting portion. Furthermore, since the inner space of the inserting portion 14 can be utilized efficiently nevertheless the outer diameter thereof is thin, it is possible to make the diameter of the suction channel 28 large. Therefore, even if the suction pressure is low, the aspiration rate thereby becomes high, and thus the wall of cavity of the living body is hardly sucked onto the suction tube.

FIGS. 6A–6D are schematic views illustrating a second embodiment of the apparatus according to the present invention. The basic structure thereof is same as that of the first embodiment, but it is arranged that the diameter of the air and water supply channel 27 is made larger so that the air and water can be supplied into the cavity of the living body more efficiently.

Figure 6A:
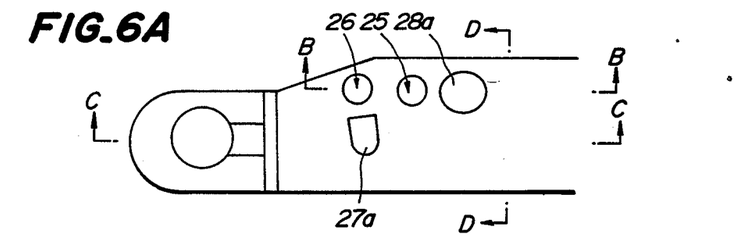
FIGS. 6A-6D are schematic views illustrating a second embodiment of the ultrasonic diagnostic apparatus according to the present invention.
Figure 6B:
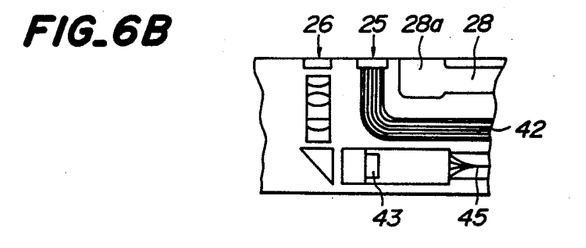
Figure 6C:
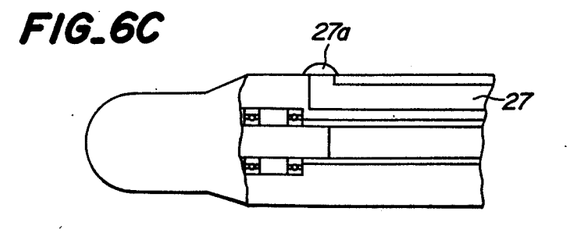
Figure 6D:
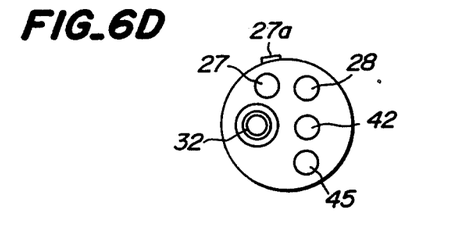

In the second embodiment, the flexible shaft 32 connected to the rotator 23 and the air and water supply channel 27 are arranged vertically in order in the left hand half of the inserting portion as shown in the sectional view of FIG. 6D, which is corresponding to FIG. 4F, and the signal cable 45 connected to the solid state image sensor 43 of the observing system 26, the light guide 42 constituting the illuminating system 25 and the suction channel 28 are arranged vertically in order in the right hand half of the inserting portion. FIG. 6B is a cross-sectional view cut along B≤B line, FIG. 6C is a cross-sectional view cut along C—C line, and FIG. 6D is a cross-sectional view cut along D—D line, respectively in FIG. 6A. In the present embodiment, the diameter of the air and water supply channel 27 can the first embodiment. Therefore, when ultrasonic diagnose is effected by filling the cavity with the degassed water, the time for supplying the degassed water can be shortened and thus the diagnosing time can be also shortened.

Figure 7:
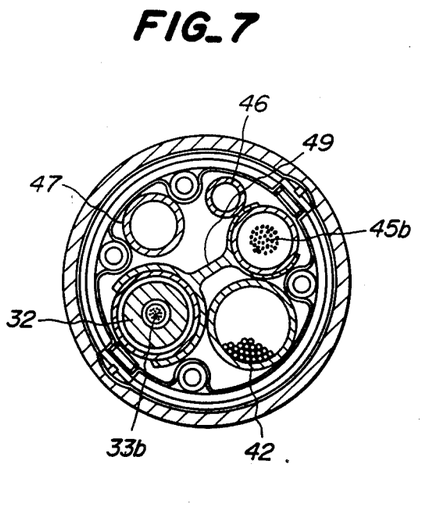
FIG. 7 is a schematic view Showing a third embodiment of the ultrasonic diagnostic apparatus according to the present invention.

FIG. 7 is a cross-sectional view representing the inserting portion of a third embodiment of the apparatus according to the present invention. The basic construction is same as that of the first embodiment, but there is provided a spacer 49 between the first signal cable 45b connected to the solid state image sensor constituting the observing system and the second signal cable 33b connected to the ultrasonic vibrating element and arranged within the flexible shaft 32, such that these two signal cables are separated from each other as far as possible. Thus the effect that the induction noise generated in each cables is reduced can be kept over the long period of time.

The present invention is not limited to the above-stated embodiments. In the above embodiments, the ultrasonic vibrating element is rotated, but it may be fixed and a reflecting mirror may be rotated as shown in FIGS. 2A and 2B. Further a motor for driving the rotator and a detector for detecting the rotating position of the rotator may be arranged in the distal end portion of the inserting portion of the apparatus. It may be also possible to provide a balloon at the distal end of the inserting portion. In this case slits for fastening the balloon may be formed in the hard top portion and the cover.

In the embodiments stated in the above, the cover 24 is formed in the cylindrical shape. However, in case of secta-scanning the object in order to obtain the ultrasonic image having a secta angle smaller than 360°, it may be possible to make only a part of the cover as a window through which the ultrasonic wave propagates, so as to form a part of cylindrical shape and the other part may be formed in any desired shape. However, in this case, the center of curvature of the window formed as a part of cylindrical shape should be coincident with the rotating center of the rotator.

It may be possible to reverse the positions of each tubes illustrated in FIGS. 4D and 4F. And it may be also possible to arrange a small lamp or a high brightness LED in the distal end of the inserting portion instead of the light guide.

As explained above, according to the present invention, the ultrasonic image is displayed on the screen of the monitor without influenced by the multiple echoes due to the refraction of the ultrasonic beam at the cover, and the uniform resolving power with respect to all scanning directions in which the ultrasonic beam is transmitted can be obtained without a complicated construction of the apparatus. Furthermore, there is no artifact due to the refraction and reflection of the ultrasonic beam at the cover and thus the position of the image displayed on the screen of the monitor is no more deviated from the actual position. Therefore, the proper ultrasonic image is displayed on the screen and thus the highly precious ultrasonic diagnostication can be realized. And also, since the first signal cable connected to the solid state image sensor and the second signal cable connected to the ultrasonic vibrating element are arranged separately at diagonally opposing positions in the inserting portion of the apparatus, even if the solid state image sensor and the ultrasonic vibrating element are driven at the same time, the optical and ultrasonic images having no inductive noise are displayed on the screen of the monitor. And, the apparatus is formed as the side view type or perspective view type but the necessary members are arrange effectively in the distal end portion of the inserting portion of the apparatus, therefore the outer diameter of the inserting portion can e made thin so that the inserting portion can be inserted into the cavity smoothly. The outer diameter of the tip portion is thinner than that of the hard portion of the inserting portion, but since the outer surfaces thereof are connected by the smoothly curved surface there is no problem to insert and operate the inserting portion.

What is claimed is:

1. An ultrasonic diagnostic apparatus comprising:
   an inserting portion having distal and proximal ends and a center axis at said distal end;
   an ultrasonic wave transmitting and receiving means having an ultrasonic vibrating element arranged at the distal end of the inserting portion for transmitting and receiving an ultrasonic wave for scanning an object to be inspected along a plane that crosses at substantially right angles with respect to an axis of the inserting portion;
   a cover arranged at the distal end of said inserting portion and having a window, said window having a preformed curvature through which the ultrasonic wave transmitted by said ultrasonic vibrating element exits toward the object and the ultrasonic wave reflected by the object is made incident upon said ultrasonic vibrating element;
   a rotating means connected to said ultrasonic wave transmitting and receiving means for rotating at least a part of said ultrasonic wave transmitting and receiving means about an axis of rotation to scan the object along said plane;
   an illuminating system for illuminating the object; and
   an observing system for forming an optical image of said object;
   whereby the axis of said inserting portion at said distal end is arranged to be deviated from said rotating axis of said ultrasonic wave transmitting and receiving means in a radial direction with respect to said rotating axis; and said center of curvature of said window is arranged to be coincident with the rotating axis of said ultrasonic wave transmitting and receiving means.

2. An ultrasonic diagnostic apparatus according to claim 1, wherein said rotating means comprises:
   a shaft arranged within said inserting portion and having one end connected to said ultrasonic wave transmitting and receiving means; and
   a driving motor arranged in a housing connected to the proximal end of said inserting portion and having a rotational output shaft connected to the other end of the shaft.

3. An ultrasonic diagnostic apparatus according to claim 2, wherein said ultrasonic wave transmitting and receiving means comprises:
   an ultrasonic vibrating element;
   a rotator connected to the one end of said shaft and supporting the ultrasonic vibrating element; and
   bearing means for supporting said rotator rotatably.

4. An ultrasonic diagnostic apparatus according to claim 3, wherein said observing system comprises an image guide.

5. An ultrasonic diagnostic apparatus according to claim 4, wherein said image guide constituting the observing system, a light guide constituting the illuminating system and said shaft are arranged to be opposite to each other viewed in a plane perpendicular to the inserting axis of the inserting portion.

6. An ultrasonic, diagnostic apparatus according to claim 5, further comprising an observation window of the observing system and an illumination window of the illuminating system both formed in a side wall of the inserting section.

7. An ultrasonic diagnostic apparatus according to claim 3, wherein said observing system comprises a solid state image sensor.

8. An ultrasonic diagnostic apparatus according to claim 7, wherein a first signal cable connected to said solid state image sensor and extending up to an operation unit connected to the proximal end of the inserting portion, the light guide constituting the illuminating system, and said shaft are arranged to be opposite to each other viewed in a plane perpendicular to the inserting axis of the inserting portion.

9. An ultrasonic diagnostic apparatus according to claim 8, further comprising an observing window of said observing system both provided in the side wall of the inserting portion.

10. An ultrasonic diagnostic apparatus according to claim 8, further comprising a second signal cable said first signal cable and said second signal cable are arranged suCh that core conductors of said cables are placed at diagonally opposing positions viewed in a plane that crosses at substantially right angles with the inserting direction of the inserting portion.

11. An ultrasonic diagnostic apparatus according to claim 10, wherein a spacer for supporting and fixing said first and second signal cables in position is arranged between said first and second cables.

12. An ultrasonic diagnostic apparatus according to claim 10, wherein said apparatus further comprises an air and water supply tube arranged between said first and second signal cables.

* * * * *